US011559152B2

(12) United States Patent
Monico (10) Patent No.: US 11,559,152 B2
(45) Date of Patent: Jan. 24, 2023

(54) PRONE POSITION PILLOW SYSTEM

(71) Applicant: DSAGA Food & Packaging Products LLC, Yorba Linda, CA (US)

(72) Inventor: Gustavo Monico, Laguna Hills, CA (US)

(73) Assignee: DSAGA FOOD & PACKAGING PRODUCTS LLC, Yorba Linda, CA (US)

( * ) Notice: Subject to any disclaimer, the term of this patent is extended or adjusted under 35 U.S.C. 154(b) by 127 days.

(21) Appl. No.: 16/931,356

(22) Filed: Jul. 16, 2020

(65) Prior Publication Data

US 2021/0330102 A1    Oct. 28, 2021

Related U.S. Application Data (60) Provisional application No. 63/014,650, filed on Apr. 23, 2020.

(51) Int. Cl.
*A47G 9/10*    (2006.01)

(52) U.S. Cl.
CPC .......... *A47G 9/1054* (2013.01); *A47G 9/1009* (2013.01)

(58) Field of Classification Search
CPC combination set(s) only.
See application file for complete search history.

(56) References Cited

U.S. PATENT DOCUMENTS

| | | | |
|---|---|---|---|
| 5,632,050 A * | 5/1997 | Zajas | A47C 20/026 5/640 |
| 5,652,981 A * | 8/1997 | Singer-Leyton | A47C 20/026 5/657 |
| 6,175,979 B1 * | 1/2001 | Jackson | A47G 9/1027 5/651 |
| 9,131,792 B1 * | 9/2015 | Wagner | A47G 9/1063 |
| 2015/0223622 A1 * | 8/2015 | Mobley | A47G 9/1054 5/636 |
| 2016/0081485 A1 * | 3/2016 | Tovar | A47C 20/025 5/631 |
| 2019/0045950 A1 * | 2/2019 | Smith | A47G 9/10 |
| 2019/0208920 A1 * | 7/2019 | Lee | A47C 31/105 |
| 2019/0254570 A1 | 8/2019 | Shinar et al. | |

FOREIGN PATENT DOCUMENTS

| | | |
|---|---|---|
| CN | 110236517 A | 9/2019 |
| JP | 2008167898 A | 7/2008 |
| JP | 2011240098 A | 12/2011 |
| JP | 2014158604 A | 9/2014 |
| JP | 6089239 B2 * | 3/2017 |

* cited by examiner

*Primary Examiner* — David R Hare
*Assistant Examiner* — Adam C Ortiz
(74) *Attorney, Agent, or Firm* — Fish IP Law, LLP (57) ABSTRACT

A prone position pillow system has a head support portion, an elongated torso component with a cavity, and an insert pillow that can be inserted into the cavity to form an empty space below. The torso component includes a sagittal oriented face hole and an air tunnel having side openings sized and dimensioned to allow a patient to insert hands into the space below the face hole. A travel pillow rests on the head support portion to support a user's face. An adjustable leg elevation component and a cylindrical component support the user's legs in a comfortable position. The head support portion has one or more grooves that can hold a breathing tube. The torso component can have a second cavity designed to create space for the user's genital area.

19 Claims, 14 Drawing Sheets

PRONE POSITION PILLOW SYSTEM

This application claims the benefit of priority of U.S. Provisional Application No. 63/014,650, filed on Apr. 23, 2020. These and all other referenced extrinsic materials are incorporated herein by reference in their entirety.

FIELD OF THE INVENTION

The field of the invention is pillow.

BACKGROUND

The following description includes information that may be useful in understanding the present invention. It is not an admission that any of the information provided herein is prior art or relevant to the presently claimed invention, or that any publication specifically or implicitly referenced is prior art.

Difficulty breathing while laying down is a common problem that reduces sleep quality and may lead to snoring while sleeping as well as fatigue and drowsiness during the day. In some cases, difficulty breathing while laying down is caused by an underlying medical condition, for example, sleep apnea syndrome, where the patient has difficulty breathing during sleep due to blocked air passage. The difficulty in breathing is also a pressing issue during the COVID-19 pandemic. The problem is exacerbated by the lack of ventilators in medical facilities, both in the US and worldwide.

It turns out that laying in a supine position (i.e., lying face up) makes breathing more difficult. In COVID-19 and sleep apnea patients, the airway collapses during a supine position, making breathing in or out more difficult, and repeatedly forcing the patient awake. However, in a prone position (i.e., lying face down), the airway tends to be more open and relaxed. In a study of patients with severe COVID-19 (SARS-CoV-2) hospitalized on ventilators, researchers found that lying face down was better for the lungs. The research letter was published online in the American Thoracic Society's American Journal of Respiratory and Critical Care Medicine.

Lying face down requires a pillow or mattress that has a downward facing opening, through which the person can breathe. U.S. Pat. No. 5,652,981 teaches a cushion for supporting a pregnant woman in a face-down position for resting, and preparatory to and during a massaging procedure. Each of Japanese patent applications JP2011240098A and JP2008167898A teaches a pillow with elongated torso and a prone breathing space. However, these pillows can be uncomfortable because they lack the mechanisms to accommodate the person's arms, shoulders, and stomach. Furthermore, these pillows do not have space for medical tubing that need to be connected to a COVID-19 patient.

Thus, there is still a need for a prone position pillow that can comfortably support the person's arms, shoulders, and stomach.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY OF THE INVENTION

The inventive subject matter provides apparatus, systems and methods in which a prone position pillow system has a head support portion, an elongated torso component with a cavity, and an insert pillow that can be inserted into the cavity to form a space below the insert pillow.

The torso component includes a sagittal oriented face hole and an air tunnel configured to communicate with the face hole. The air tunnel can open laterally, superiorly, or both. The insert pillow forms an empty space below when inserted into the cavity. The empty space is crucial for comfortably supporting a person's stomach region. The space has a volume of at least 50 $cm^3$, preferably at least 100 $cm^3$, and more preferably at least 200 $cm^3$, such that a user can rest the stomach comfortably on the torso component.

In preferred embodiments, the head support portion has a face hole with at least one opening on the side to allow air flowing in and out of the face hole. In preferred embodiments, the face hole has three side openings to enhance air flow. In especially preferred embodiments, the openings are sized and dimensioned to allow a patient to insert hands into the space below the face hole, so that the patient can relax his or her arms and shoulders. A patient laying on the pillow can have their smart phone under the face hole and text or watch movies which would provide a psychological benefit to the patient for using the pillow. Advantageously, the face hole and vent openings also allow a breathing tubing or a CPAP (Continuous Positive Airway Pressure) mask to be placed on a patient's face while in a prone position. In some embodiments, the head support portion has one or more grooves on the side of the face hole to facilitate threading breathing tubing or tubing from a CPAP mask or other breathing systems to be connected to the face or head of the person lying on the pillow.

In preferred embodiments, the prone position pillow system has a travel pillow sized and dimensioned to rest on the head support portion of the torso component. In some embodiments, the prone position pillow system has a leg elevation component that is detached from the torso component. Preferably, the leg elevation component has an inclined side that faces the torso component. In some embodiments, the prone position pillow system has a cylindrical component on top of the leg elevation component, so that it can roll to a position to best support the patient's legs.

In some embodiments, the torso component has left and right regions configured to support the user's shoulders and arms. In some embodiments, each side contouring region tilts at a first angle with respect to a horizontal plane parallel to a bottom surface of the pillow. Preferably, the first angle is between 45 and 75 degrees. In some embodiments, each side contouring region tilts at a second angle with respect to a vertical plane along a longitudinal axis of the pillow. Preferably, the second angle is between 30 and 60 degrees. In some embodiments, the prone position pillows are custom designed according to each individual user's size and preference.

In some embodiments, the prone position pillow tracks the position and/or breathing patterns of the user by having sensors on or within the headrest. The sensors can sense when the user stops breathing while sleeping and trigger a vibration mechanism of the headrest, so that the user's head is jolted which triggers the user to restart breathing.

In some embodiments, the prone position pillow has a sensor-controlled cooling mechanism. When the temperature of the pillow rises above a predetermined range, as detected by the sensor, the cooling mechanism is activated to cool the pillow to a predetermined temperature.

In some embodiments, the contemplated prone position pillow can be adapted to be used as a massage table. They can also be used in post-surgical support, including ocular surgery and back surgery.

Various objects, features, aspects and advantages of the inventive subject matter will become more apparent from the following detailed description of preferred embodiments, along with the accompanying drawing figures in which like numerals represent like components.

DETAILED DESCRIPTION

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
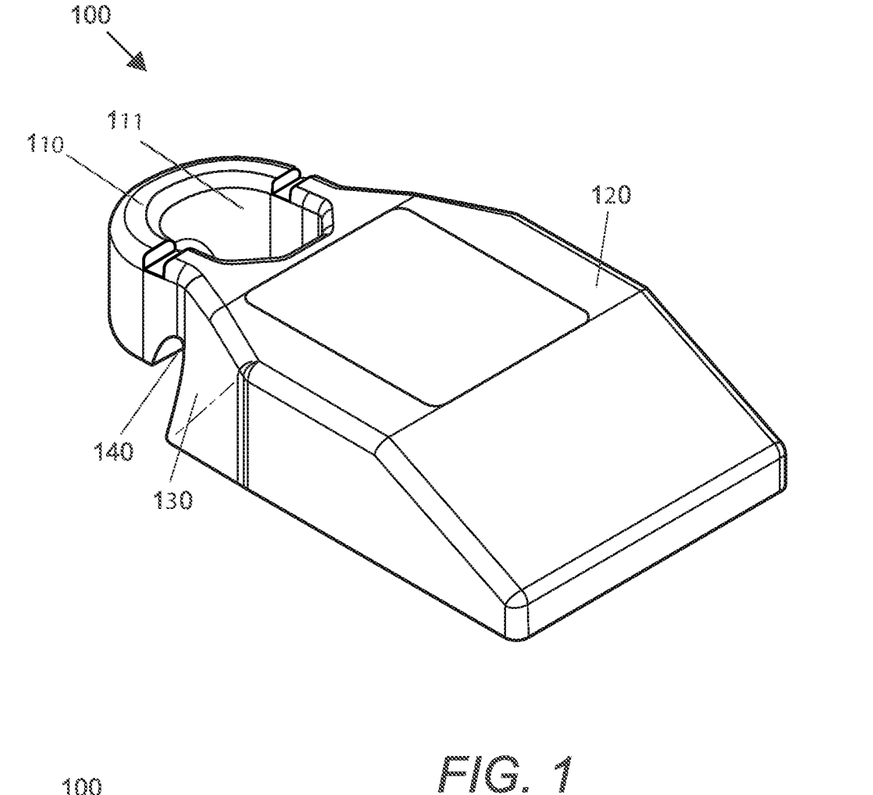
FIG. 1 shows a perspective view of an embodiment of the prone position pillow system 100.
Figure 2:
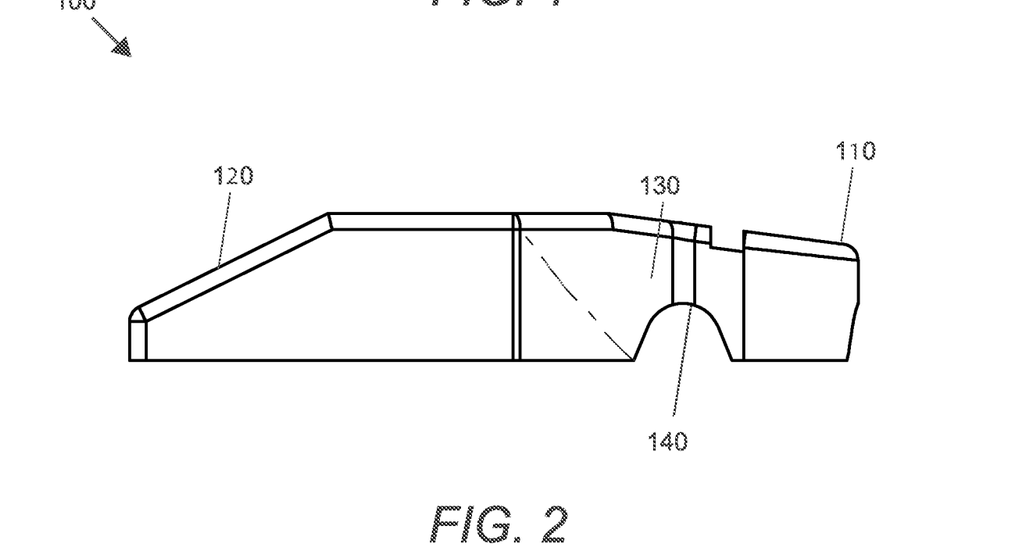
FIG. 2 shows a side view of the prone position pillow system 100 of FIG. 1.
Figure 3:
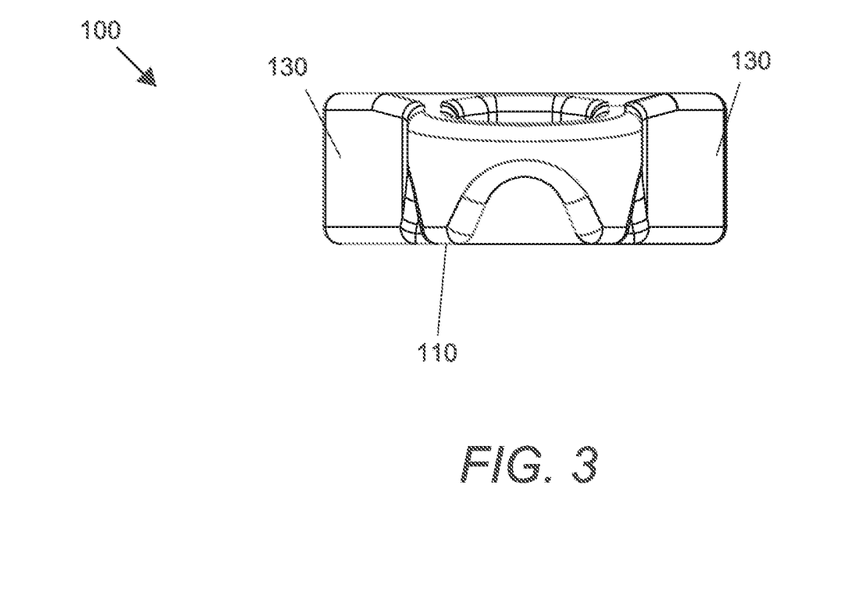
FIG. 3 shows a front view of the prone position pillow system 100 of FIG. 1.
Figure 4:
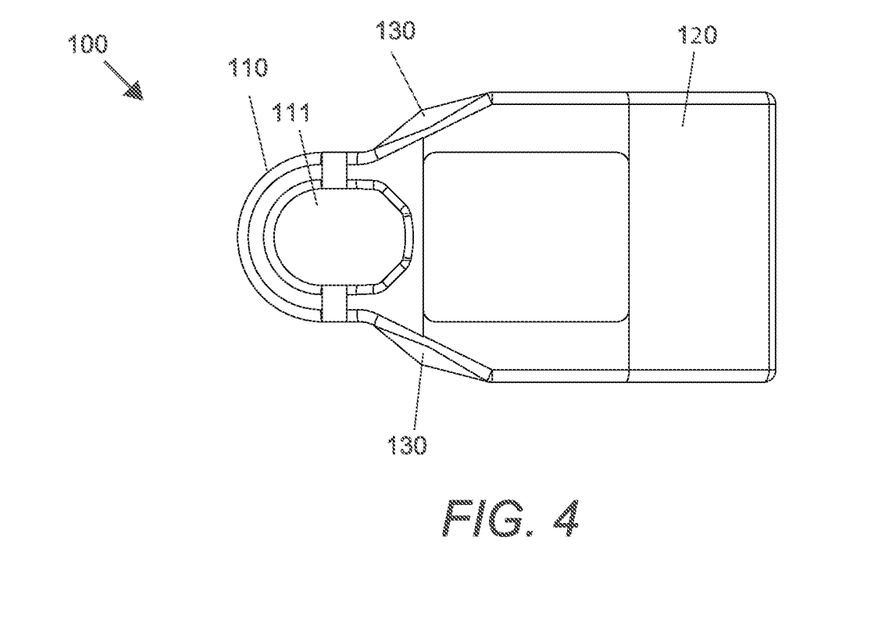
FIG. 4 shows a top view of the prone position pillow system 100 of FIG. 1.
Figure 5:
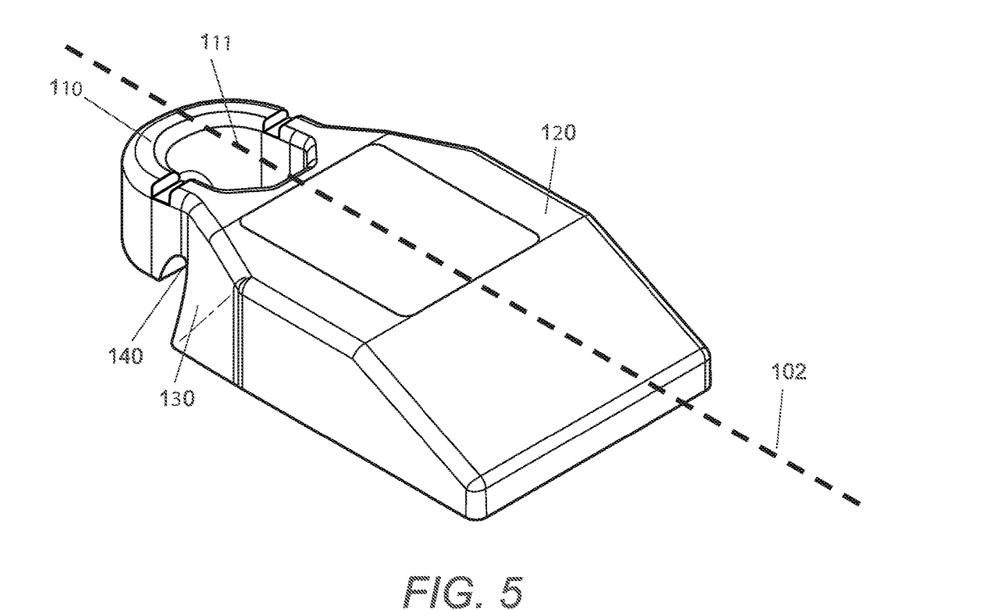
FIG. 5 shows the prone position pillow system 100 in FIG. 1, having an imaginary longitudinal axis 102 along the center of the pillow system 100.
Figure 6:
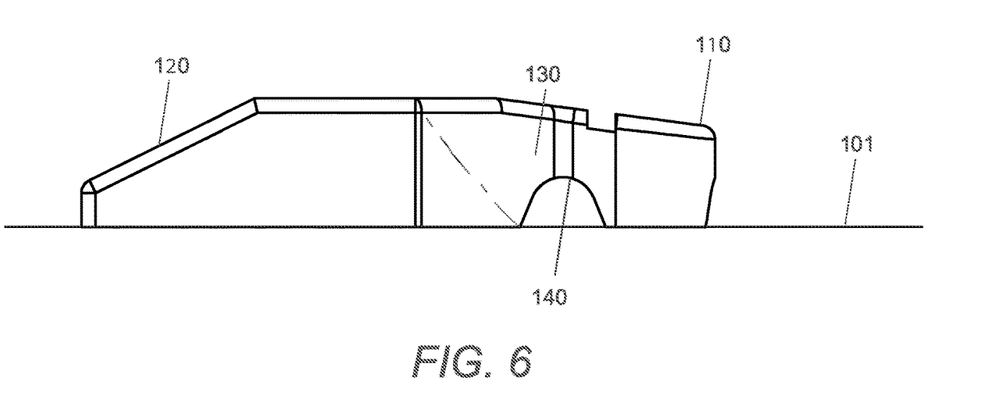
FIG. 6 shows the prone position pillow system 100 in FIG. 2, with a horizontal plane 101 under the bottom surface of the pillow system 100.
Figure 7:
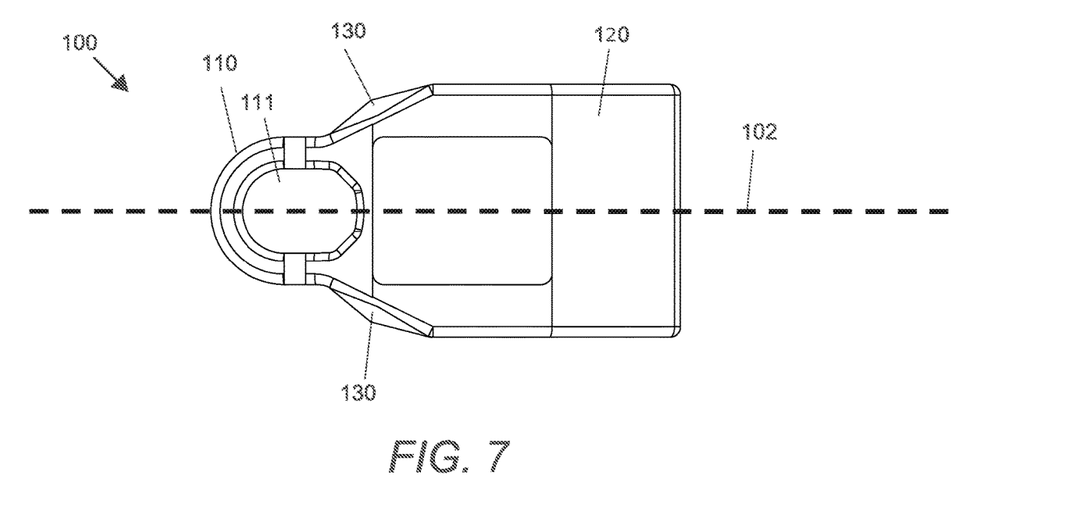
FIG. 7 shows the prone position pillow system 100 in FIG. 3, having an imaginary longitudinal axis 102 along the center of the pillow system 100.

In FIGS. 1-4, the pillow system 100 has a headrest 110 with a breathing space 111, a torso component 120, and side contouring regions 130 for the arms and shoulders. The neck region 140 of the pillow is elevated so that there is more space for the person to breathe through. Each side contouring region 130 has a substantially triangular shape that is tilting both horizontally and longitudinally. The side contouring region 130 is tilting at a first angle with respect to a horizontal plane parallel to the bottom surface (i.e., horizontally), and is also tilting at a second angle with respect to a vertical plane along the longitudinal axis (longitudinally). In preferred embodiments, the first angle is between 45 and 75 degrees, and the second angle is between 30 and 60 degrees. This combination is critical for the user's arms and shoulders to be supported comfortably. FIGS. 5 and 6 show a longitudinal axis 102 along the center of the pillow system 100. A horizontal plane 101 parallel to the bottom surface is shown in FIG. 7.

Figure 8:
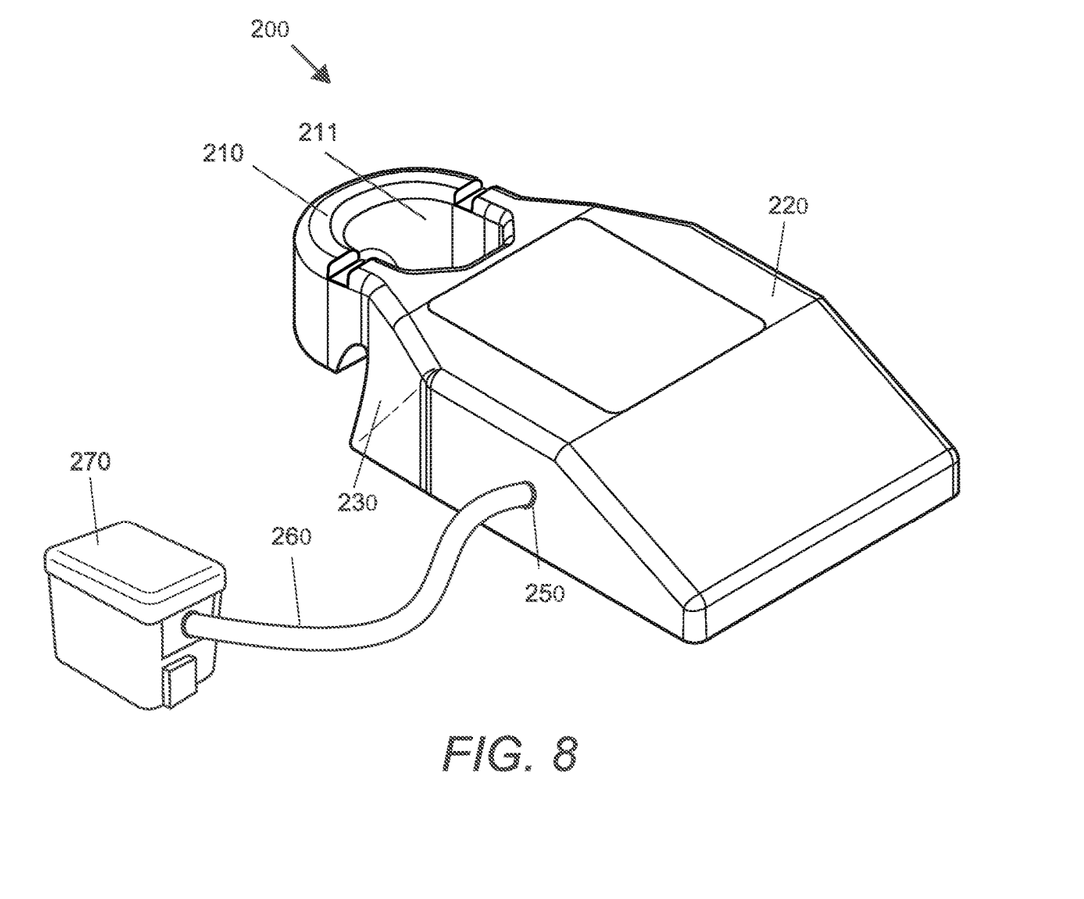
FIG. 8 shows a perspective view of a prone position pillow system 200 with a cooling device.

FIG. 8 shows a perspective view of an embodiment of the pillow 200, coupled with a cooling device 270 through a hole 250 in the pillow 200 and a hose 260. It is contemplated that the cooling device 270 can cool a liquid (e.g., water) or air that can be pumped into the pillow 200.

Figure 9:
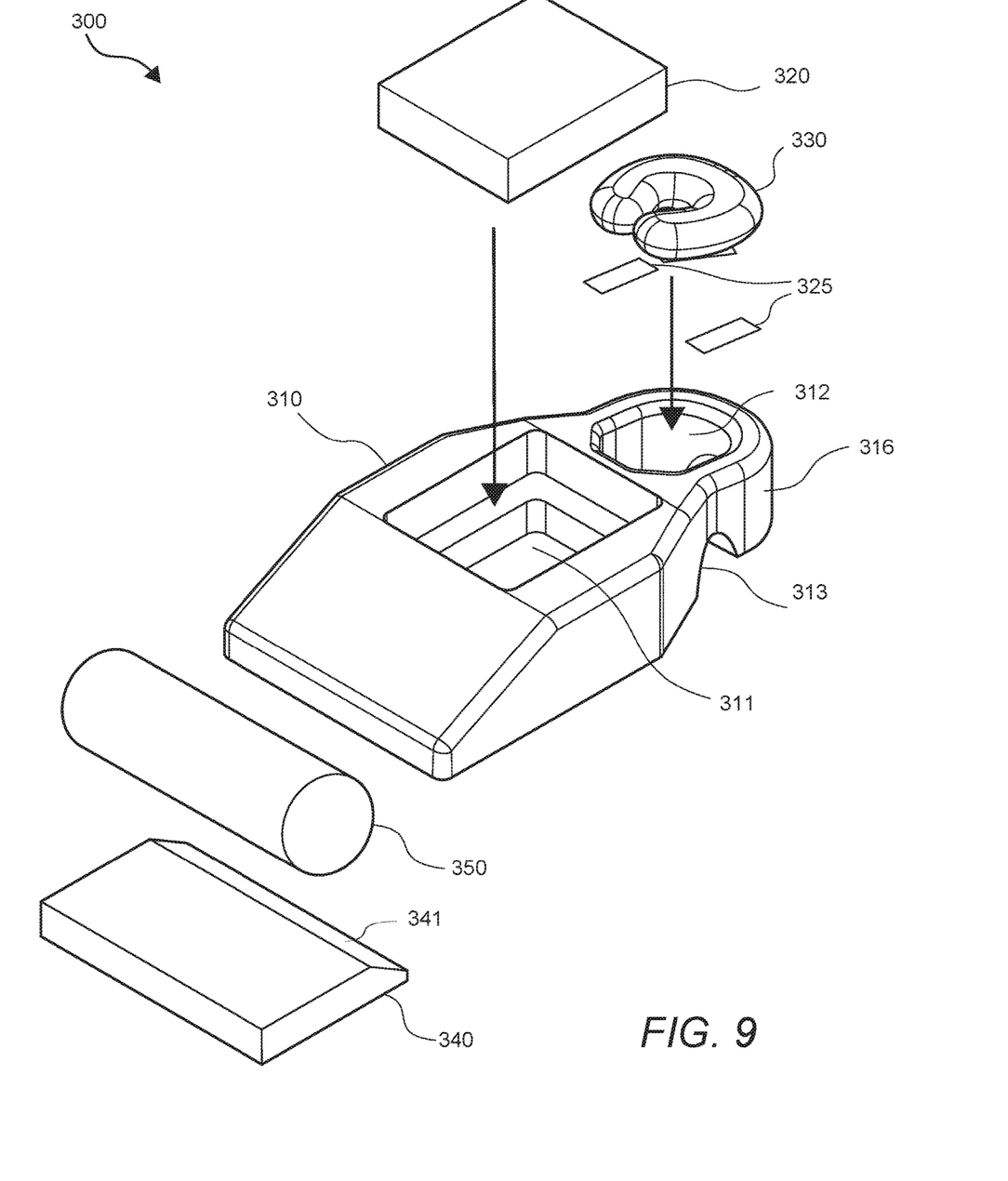
FIG. 9 shows an embodiment of a prone position pillow system 200 having a torso component, a travel pillow, an insert pillow, leg elevation component, and a cylindrical component.

In FIG. 9, a prone position pillow system 300 has an elongated torso component 310, an insert pillow 320, and a travel pillow 330. The torso component 310 supports the body weight of the patient. The torso component 310 is preferably made of a hard material, for example, urethane foam, and can be surrounded by plastic supports to strengthen the system, especially the head support portion 316. In some embodiments, the torso component 310 can also be made with a soft material, for example, memory foam. The torso component 310 has a layered cavity 311 having two layers. The insert pillow 320 can rest on the mid layer of the cavity 311 and leaves an empty space in the bottom portion of the cavity 311. When a patient lays on the insert pillow 320, it can at least partially occupy the empty space below to provide additional comfort to the patient. The insert pillow 320 is preferably made of a soft material, for example, memory foam.

A travel pillow 330 is located at the head support portion 316 of the torso component 310 on which the patient can rest his or her face. The travel pillow 330 can be attached to the torso component 310 using Velcro® strips 325, so that the position of the travel pillow 330 can be adjusted relative to the torso component 310 as desired by the patient. The travel pillow 330 can be made preferably of a soft material (e.g., memory foam). A soft material provides a comfortable support for the face to help minimize discomfort to COVID-19 patients for being placed in the prone position for extended periods of time.

The prone position pillow system 300 has a leg elevation component 340 to support a person's legs. The leg elevation component 340 has an inclined side 341 to allow the patient to comfortably rest his legs and use gravity to improve blood circulation. A cylindrical component 350 can be placed on top of the leg elevation component 340. The cylindrical component 350 can be a cylinder, preferably made of a soft material (e.g., memory foam). The distance between the leg elevation component 340 and the torso component 310 can be adjusted depending on the person's height. The leg elevation component 340 can be used to keep the patient's feet in a specific position. For example, the person's legs can be adjusted into a "neutral" position where the legs naturally extend and are relaxed. Once the legs are in the neutral position, a health care professional can test the back of the feet for reflexes (i.e., abnormal plantar reflex, or Babinski reflex, etc.) A positive reflex test result may indicate the patient is recovering from COVID-19, while a negative test may indicate the patient is not recovering from COVID-19.

Figure 11:
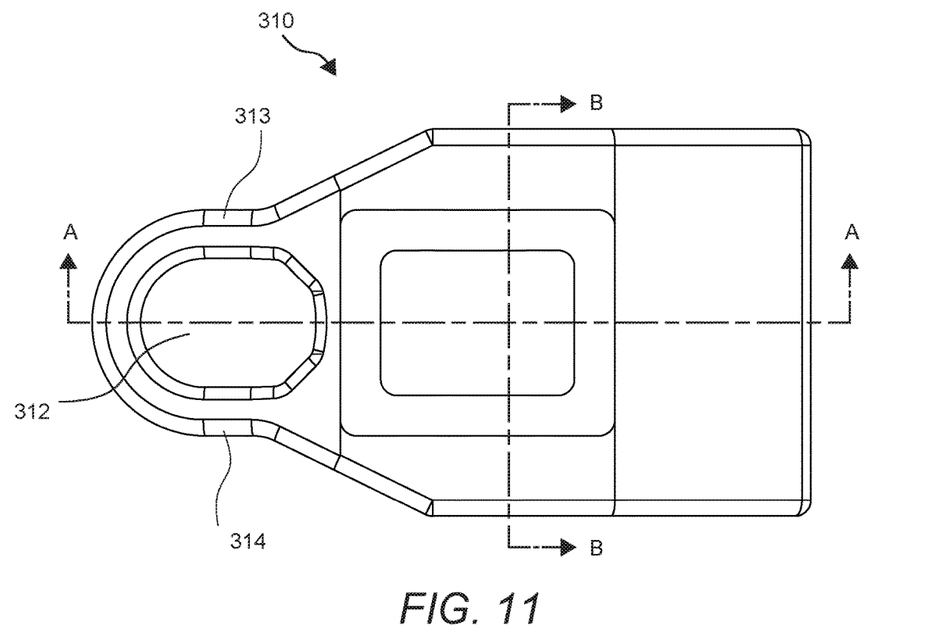
FIG. 11 shows a top view of the torso component in FIG. 10.
Figure 12:
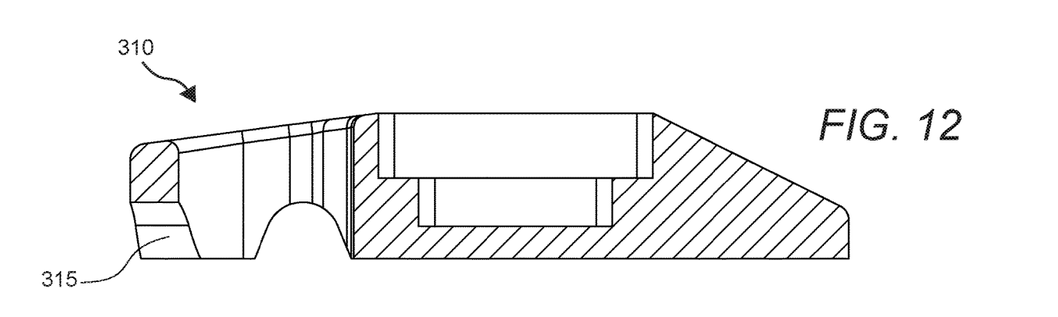
FIG. 12 shows a cross-sectional view of the torso component in FIG. 11, along plane A-A.
Figure 13:
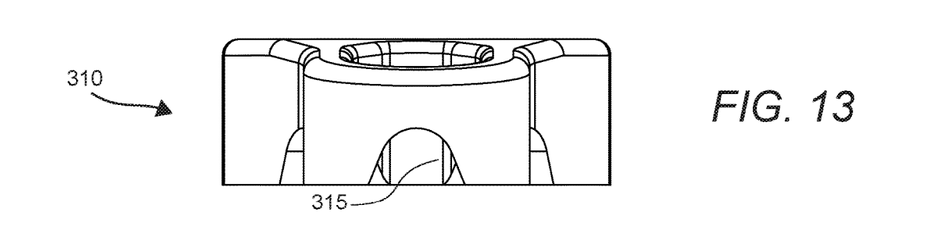
FIG. 13 shows a front view of the torso component in FIG. 10.

In preferred embodiments, the head support portion 316 of the torso component 310 has a sagittal oriented face hole 312 and an air tunnel configured to communicate with the face hole 312. The air tunnel has a right lateral opening 313, a left lateral opening 314, and a superior opening 315 (also shown in FIGS. 11-13). The openings 313 and 314 are sized and dimensioned to allow a patient to insert his or her hands and forearms inside the space below the face hole 312. The face hole 312 keeps the person's nose and mouth area free of contact while in the prone position. This is ideal for COVID-19 patients who complain of sores and pain after lying face down on a regular hospital bed mattress while wearing a breathing mask system (e.g., CAPA mask in FIG. 17).

Figure 10:
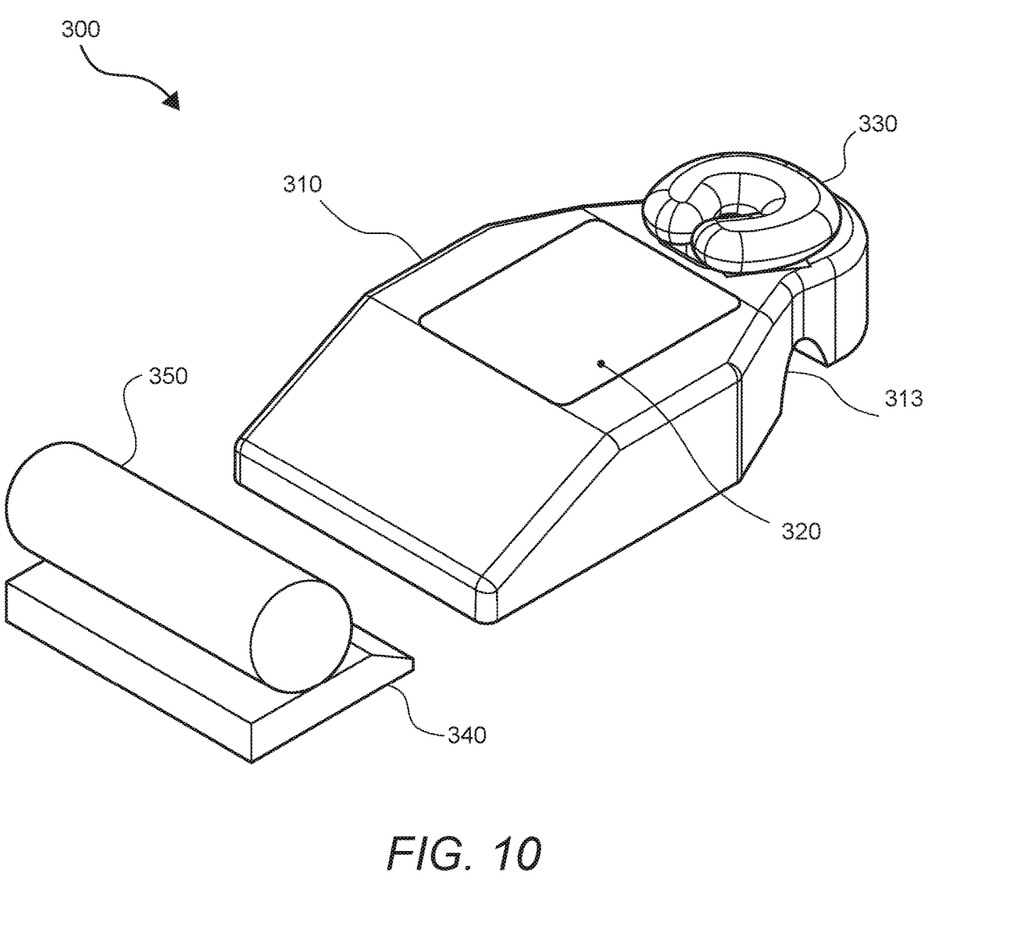
FIG. 10 shows the embodiment of pillow system 200 in FIG. 9, where the insert pillow is inserted into the cavity of the torso component.

FIG. 10 shows the prone position pillow system 300 in FIG. 9, where the insert pillow 320 is inserted into the cavity 311 in the torso component 310, and the travel pillow 330 is placed on the head support portion 316 of the torso component 310.

Figure 14A:
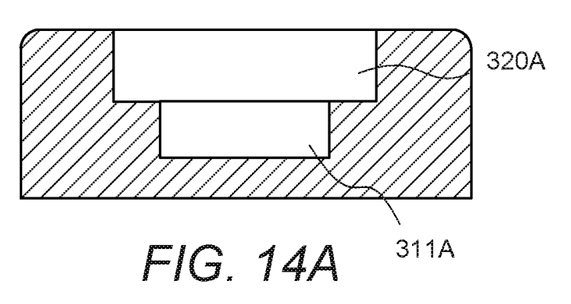
FIG. 14A shows a cross-sectional view of the torso component in FIG. 11, along plane B-B.
Figure 14B:
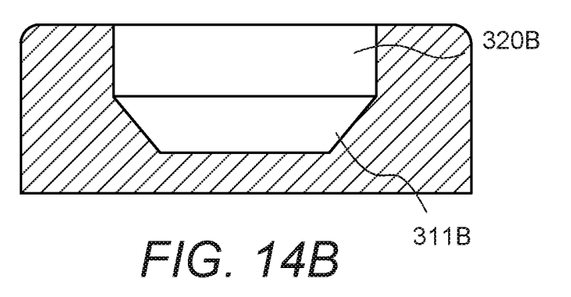
FIG. 14B shows a cross-sectional view of a modified torso component in FIG. 14A, with a cavity of a graduate narrowing.
Figure 14C:
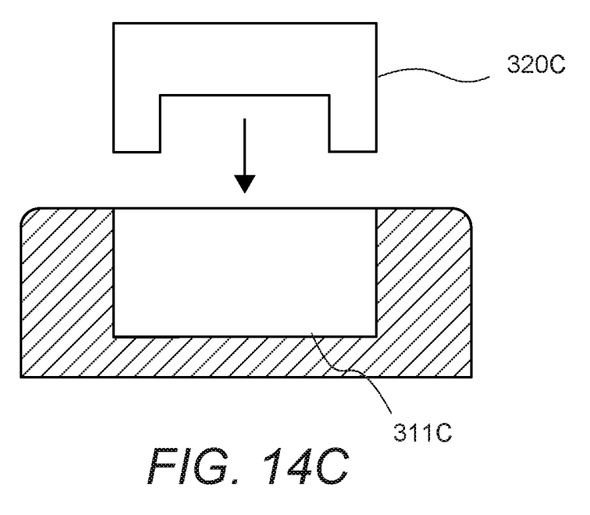
FIG. 14C shows a cross-sectional view of a modified torso component in FIG. 14A with a rectangular cavity, and a modified insert pillow having a cavity.

In FIG. 14A, the cavity 311A is broader at the top than at the bottom, with a sharp narrowing in the middle, such that the insert pillow 320A can be supported and form an empty space below when inserted into the cavity 311A. In FIG. 14B, the cavity 311B narrows gradually. When insert pillow 320B is inserted into the cavity 311B, there will still be an empty space since the side wall of the cavity 311B will support the insert pillow 320B. In FIG. 14C, the cavity 311C has a rectangular shape. The insert pillow 320C has a cavity, and thus creates an empty space when inserted into the rectangular cavity 311C.

Figure 15A:
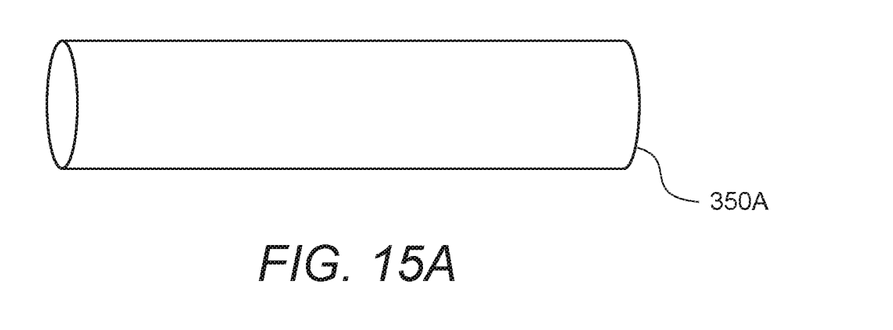
FIG. 15A shows the cylindrical component in FIG. 9.
Figure 15B:
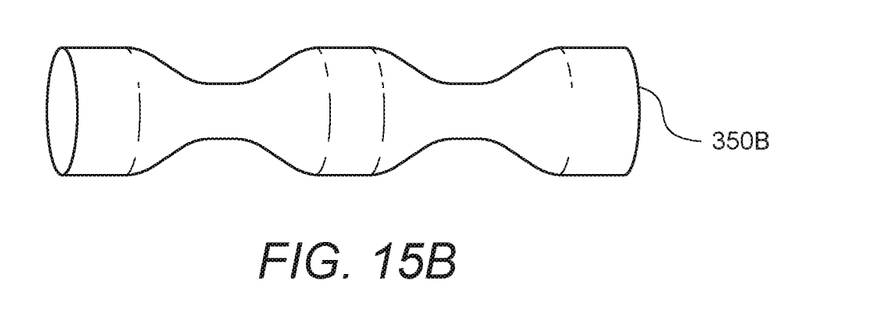
FIG. 15B shows a variation of the cylindrical component in FIG. 15A.
Figure 15C:
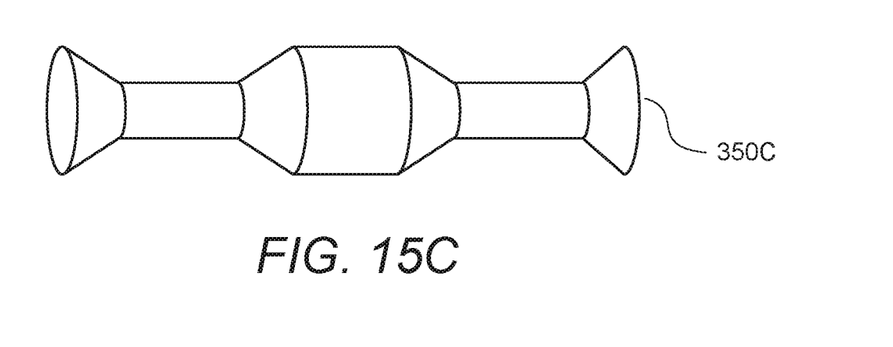
FIG. 15C shows another variation of the cylindrical component in FIG. 15A.

FIG. 15A shows the cylindrical component 350A in FIG. 9. In FIG. 15B, the cylindrical component 350B is narrowed on two locations to accommodate a person's legs. In FIG. 15C, the cylindrical component 350C is also narrowed on two locations to accommodate a person's legs.

Figure 16:
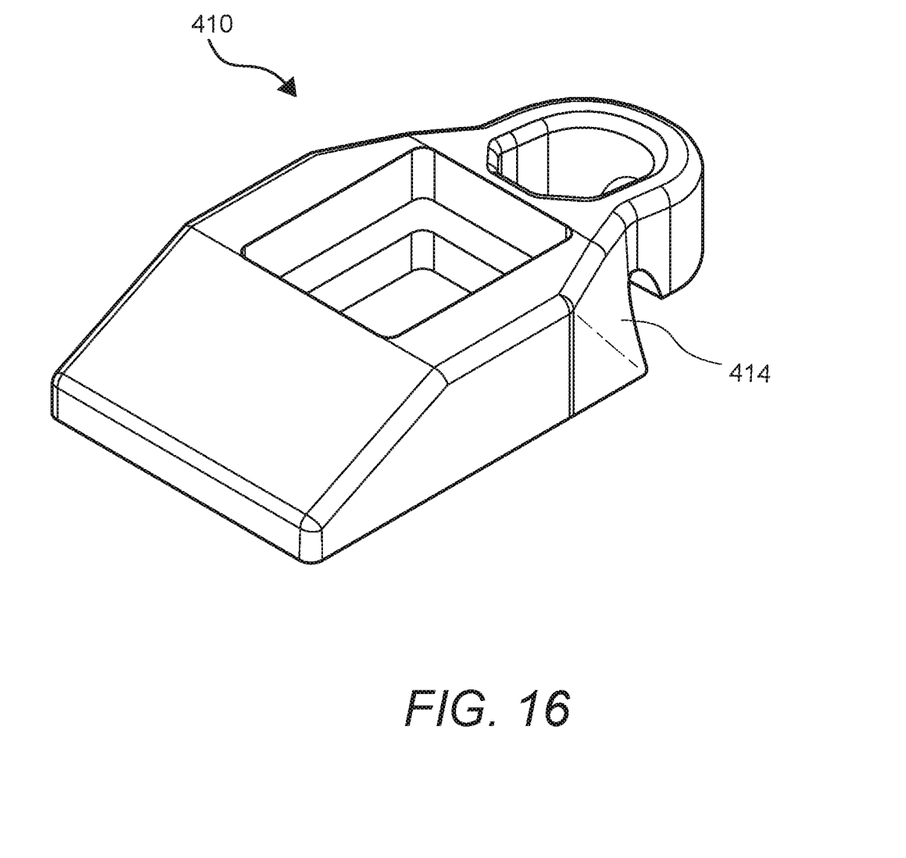
FIG. 16 shows another embodiment of pillow system 300 having tilted shoulder regions.

FIG. 16 shows another embodiment of pillow system 410 having tilted shoulder regions (e.g., 414 on the right side, left side is symmetrical to the right (not shown)). The right shoulder region 414 has a substantially triangular shape that is tilting both horizontally and longitudinally. The right shoulder region 414 is tilting at a first angle with respect to a horizontal plane parallel to the bottom surface (i.e., horizontally), and is also tilting at a second angle with respect to a vertical plane along the longitudinal axis (longitudinally). In preferred embodiments, the first angle is between 45 and 75 degrees, and the second angle is between 30 and 60 degrees. This combination is critical for the user's arms and shoulders to be supported comfortably.

Figure 17:
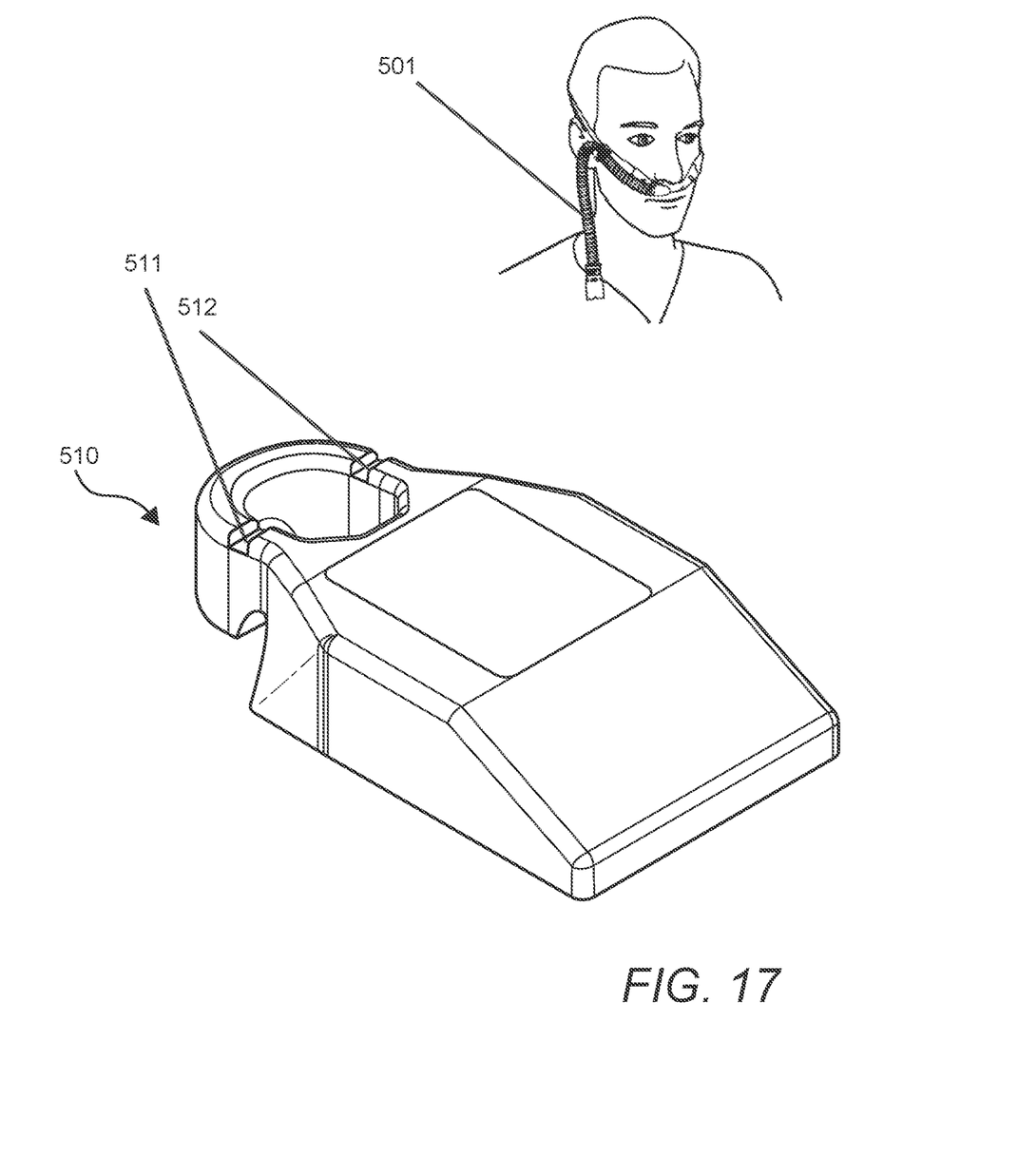
FIG. 17 illustrates a torso component 510 having grooves positioned to hold a breathing tube of a breathing system (e.g., CPAP mask).

FIG. 17 shows a torso component 510 having two grooves 511 and 512 at the head support portion, on each side of the face hole. The grooves 511 and 512 are sized and dimensioned to fit a breathing tube 501 of a breathing system (e.g., CPAP mask).

Figure 18:
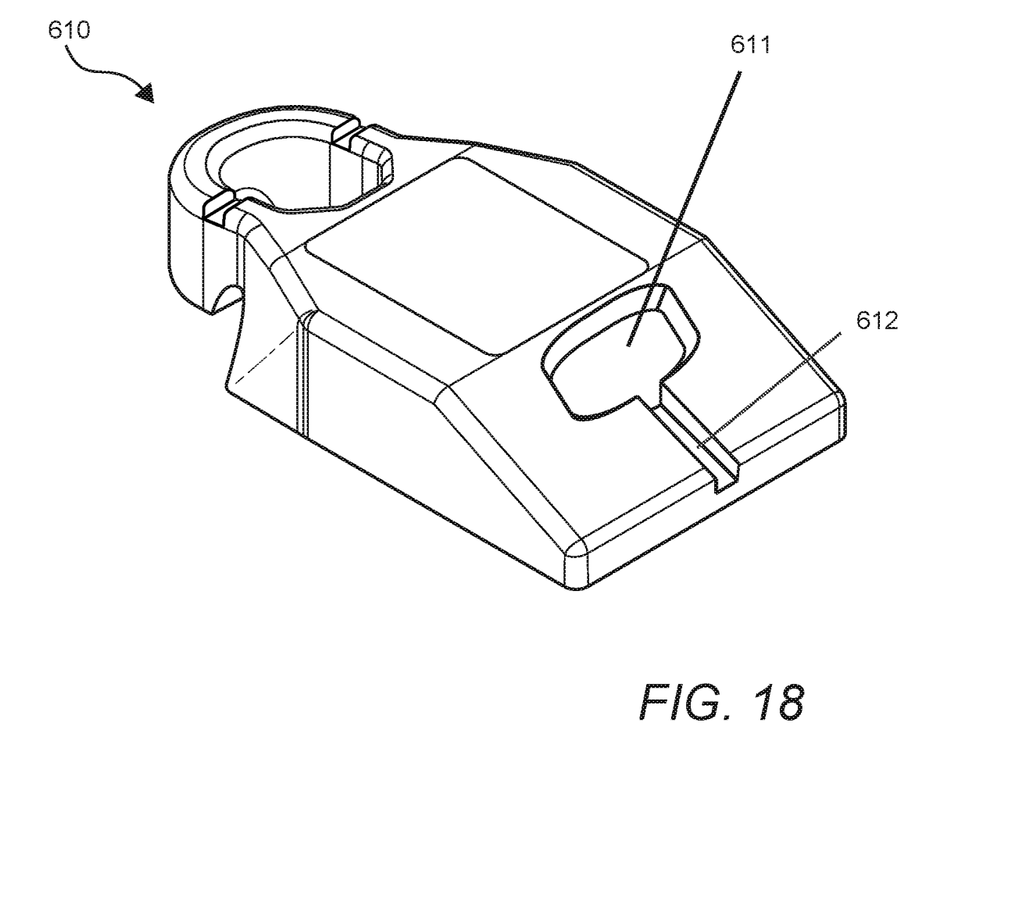
FIG. 18 shows another embodiment of a torso component having a second cavity that creates additional space for a user's genital area.

FIG. 18 shows another embodiment of a torso component 610 having a second cavity 611 that is located at an inclined surface of the torso component 610. This second cavity 611 creates additional space for the user's genital area, especially when the user has medical devices connected to his/her genital area (e.g., to collect urine). Additionally, a channel 612 is connected to the second cavity 611 such that medical tubes can go through the channel 612.

Figure 19:
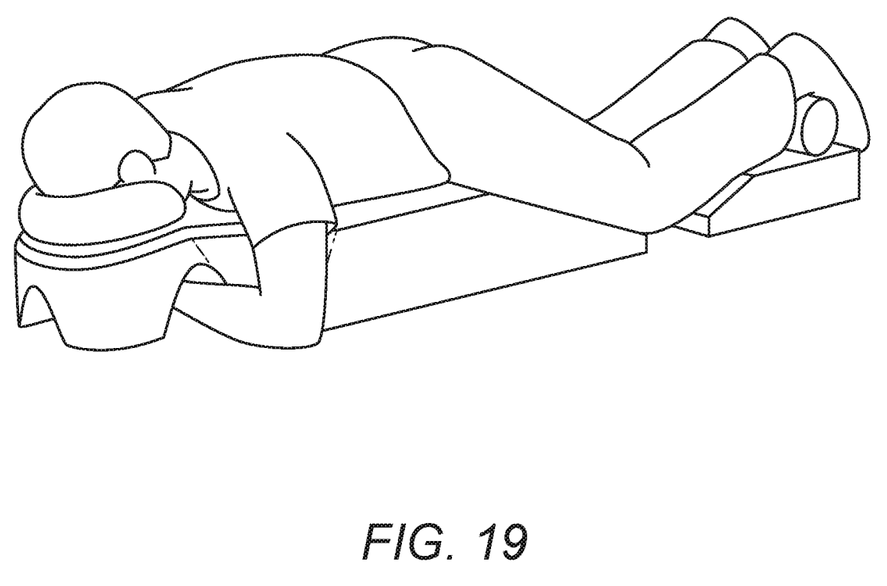
FIG. 19 shows a user laying on a pillow system with hands and forearms inserted into the pillow system.

FIG. 19 shows a person laying on a prone position pillow system (e.g., 300) with his body supported by the pillow system, including torso, arms, shoulders, legs and feet. The person's hands and forearms are tucked into the pillow system.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A prone position pillow system, comprising: an elongated torso component configured to support a user's torso comprising: 1) a first cavity extending downwards from a top surface of the torso component and having a narrowed portion below a depth within the cavity, and wherein the first cavity comprises a first volume above the depth and a second volume below the depth, further comprising an insert pillow support surface within the cavity and located at the depth, and 2) a head support portion comprising a sagittal oriented face hole; an insert pillow sized and dimensioned to fill the first volume such that when the insert pillow is inserted into the first cavity, the second volume remains as empty space below a bottom surface of the insert pillow, and wherein the insert pillow rests on the insert pillow support surface when inserted into the first cavity.

2. The prone position pillow system in claim 1, wherein the first cavity narrows gradually to form the narrowed portion.

3. The prone position pillow system in claim 1, wherein the first cavity narrows sharply to form the narrowed portion.

4. The prone position pillow system in claim 1, wherein the second volume remains as empty space measuring at least 50 cm$^3$.

5. The prone position pillow system of claim 1, further comprising an air tunnel configured to communicate with the face hole.

6. The prone position pillow system of claim 5, wherein the air tunnel opens laterally.

7. The prone position pillow system of claim 5, wherein the air tunnel opens superiorly.

8. The prone position pillow system of claim 5, wherein the air tunnel comprises a left opening and a right opening, sized and dimensioned to allow a person to insert hands and a portion of arms into the openings.

9. The prone position pillow system of claim 1, further comprising a travel pillow sized and dimensioned to rest on the head support portion of the torso component.

10. The prone position pillow system of claim 1, further comprising a leg elevation component, detached from the torso component.

11. The prone position pillow system of claim 10, wherein the leg elevation component comprises an inclined side that faces the torso component.

12. The prone position pillow system of claim 10, further comprising an at least partially cylindrical component on top of the leg elevation component.

13. The prone position pillow system of claim 1, wherein the torso component further comprises left and right side contouring regions on left and right outer sidewalls, respectively, configured to support a user's shoulders and arms.

14. The prone position pillow system of claim 13, wherein each side contouring region tilts at an angle with respect to a horizontal plane parallel to a bottom surface of the pillow.

15. The prone position pillow system of claim 14, wherein the angle is between 45 and 75 degrees.

16. The prone position pillow system of claim 13, wherein each side contouring region tilts at an angle with respect to a vertical plane along a longitudinal axis of the pillow.

17. The prone position pillow system of claim 16, wherein the angle is between 30 and 60 degrees.

18. The prone position pillow system of claim 1, wherein the head support portion comprises a groove on the top surface of the torso component, sized and dimensioned to hold a breathing tube.

19. The prone position pillow system of claim 1, wherein the torso component comprises a second cavity extending downwards from the top surface of the torso component, and wherein the first and second cavities are disposed on different portions of the torso component.

* * * * *